(12) United States Patent
Knight

(10) Patent No.: US 7,431,733 B2
(45) Date of Patent: Oct. 7, 2008

(54) VASCULAR PROSTHESIS

(75) Inventor: Joseph Allen Knight, Palm Harbor, FL (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 10/561,929

(22) PCT Filed: Jun. 28, 2004

(86) PCT No.: PCT/US2004/021046

§ 371 (c)(1),
(2), (4) Date: Jun. 2, 2006

(87) PCT Pub. No.: WO2005/000168

PCT Pub. Date: Jan. 6, 2005

(65) Prior Publication Data

US 2006/0271167 A1 Nov. 30, 2006

Related U.S. Application Data

(60) Provisional application No. 60/483,035, filed on Jun. 27, 2003.

(51) Int. Cl.
*A61F 2/24* (2006.01)
(52) U.S. Cl. ........................ 623/2.1; 623/2.17; 623/2.18
(58) Field of Classification Search .......... 623/2.1–2.38
See application file for complete search history.

(56) References Cited

U.S. PATENT DOCUMENTS

| 4,451,936 A | | 6/1984 | Carpentier et al. |
| 4,892,540 A | | 1/1990 | Vallana |
| 5,139,515 A | | 8/1992 | Robicsek |
| 6,074,419 A | * | 6/2000 | Healy et al. ................ 623/2.14 |
| 6,197,143 B1 | | 3/2001 | Bodnar |
| 6,352,554 B2 | | 3/2002 | De Paulis |
| 6,364,905 B1 | | 4/2002 | Simpson et al. |
| 6,375,679 B1 | | 4/2002 | Martyn et al. |
| 6,461,382 B1 | | 10/2002 | Cao |
| 6,540,781 B2 | * | 4/2003 | Adams ...................... 623/2.13 |
| 6,544,285 B1 | * | 4/2003 | Thubrikar et al. .......... 623/2.12 |
| 6,875,230 B1 | | 4/2005 | Morita et al. |

(Continued)

FOREIGN PATENT DOCUMENTS

EP  1 230 901 A1  8/2002

(Continued)

OTHER PUBLICATIONS

Thubrikar, M. et al. *The Aortic Valve*, 1989 CRC Press, Boca Raton, FL.

(Continued)

*Primary Examiner*—Suzette J Gherbi
(74) *Attorney, Agent, or Firm*—Saliwanchik, Lloyd & Saliwanchik

(57) ABSTRACT

The subject invention concerns vascular prosthetic devices and methods for ascending aorta and/or valve replacement in humans and animals. In one embodiment, a device of the invention includes a vessel-like structure having a first end adapted for surgical attachment to a left ventricle, a second end adapted for surgical attachment to an aorta, and, interposed between the first and second ends, a sinus portion configured in the shape of the sinuses of Valsalva in a human aortic valve.

29 Claims, 5 Drawing Sheets

U.S. PATENT DOCUMENTS

| | | |
|---|---|---|
| 2001/0025196 A1 | 9/2001 | Chinn et al. |
| 2001/0049553 A1 | 12/2001 | De Paulis |
| 2002/0071902 A1 | 6/2002 | Ding et al. |
| 2002/0082689 A1 | 6/2002 | Chinn |
| 2004/0024452 A1* | 2/2004 | Kruse et al. .............. 623/2.13 |
| 2004/0062790 A1 | 4/2004 | Constantine et al. |
| 2004/0093080 A1 | 5/2004 | Helmus et al. |
| 2005/0055079 A1* | 3/2005 | Duran ..................... 623/1.13 |
| 2006/0167333 A1* | 7/2006 | Moore et al. ............... 600/16 |

FOREIGN PATENT DOCUMENTS

| | | |
|---|---|---|
| WO | WO 95/03754 | 2/1995 |

OTHER PUBLICATIONS

Thubrikar, M. et al. *The Aortic Valve*, 1989, CRC Press, Boca Raton, FL, pp. 2-10.

Bellhouse, B.J. et al. "Fluid Mechanics of the Aortic Root with Application to Coronary Flow" *Nature*, Sep. 1968, pp. 1059-1061, vol. 219.

\* cited by examiner

VASCULAR PROSTHESIS

CROSS-REFERENCE TO RELATED APPLICATION

This application is the U.S. national stage application of International patent application No. PCT/US2004/021046, filed Jun. 28, 2004, which claims the benefit of 60/483,035, filed Jun. 27, 2003.

FIELD OF THE INVENTION

The invention relates generally to the fields of biomedical engineering and vascular prosthetic grafts. More particularly, the invention relates to a prosthesis useful as a replacement for the ascending aorta and aortic sinuses and in some applications, a replacement for an aortic valve, aortic sinuses, and the ascending aorta.

BACKGROUND OF THE INVENTION

Blood flow from the left ventricle to the aorta is regulated by the aortic valve which may be tricuspid (normal) or bicuspid (pathologic). As the description suggest, the valve may include three crescent-shaped leaflets, or two leaflets, that each move between a closed position where blood cannot pass and an open position where blood can pass. In the closed position, the margins of the leaflets come together flushly to seal the passage between the left ventricle and the aorta. In the open position, each of the leaflets moves into a cavity, termed a sinus of Valsalva, allowing blood to flow through the valve orifice. Two of the sinuses include coronary ostia for the right and left coronary arteries. Because the third sinus does not contain an ostia, it is referred to as the non-coronary sinus.

Malfunction of the aortic valve can have severe clinical consequences. Replacement of the aortic valve is typically used in patients who have either or both a leakage or obstruction of the aortic valve. These conditions may result from a congenital defect or from a disease condition such as a degenerative calcification or inflammation of the aortic valve. Fortunately, surgical procedures and prostheses have been developed for replacing defective aortic valves. These procedures may involve excision of the sinuses of Valsalva and reattachment of the coronary arteries to the prosthesis at a convenient location if the ascending aorta is also involved with pathologic changes. While aortic valve replacement is usually successful, the results may be less than ideal long-term because of removal of the sinuses of Valsalva and suboptimal placement of the coronary artery anastomoses can have a negative effect on the fluid dynamics of blood flow.

Other conditions can affect the ascending aorta. For example, in Marfan's syndrome, a dilation of the aortic root (the area where the aorta meets the aortic valve) is often observed in patients. This can dilate the aortic valve, causing it to leak. Aneurysms can also occur on the aorta and sinuses of Valsalva. Treatment of these conditions may require removal and replacement of the ascending aorta while leaving the aortic valve in place.

BRIEF SUMMARY OF THE INVENTION

The subject invention relates to the development of a vascular prosthesis useful in ascending aorta replacement surgery (with or without concomitant valve replacement). The vascular prosthesis includes a portion fashioned into sinuses that resemble the sinuses of Valsalva. Ostia which serve as re-attachment sites for the left and right coronary arteries are optimally located on the sinuses. In one embodiment, a prosthesis of the invention comprises artificial or non-artificial vessels extending from the ostia to aid in coronary artery attachment, e.g., in situations where the coronary arteries are too short to reach the ostia of the prosthetic device. A vascular prosthesis of the invention can also include a valve for regulating blood flow. Prosthetic devices of the present invention are advantageous because sinuses and ostia of the devices mimic the natural anatomy of the aortic valve/ascending aortic region of a heart, and preferably allow for optimal blood flow.

In one embodiment of a prosthesis of the invention, the aortic root of a valve is attached to the bottom of the prosthesis with the valve seated inside of the prosthesis. The prosthesis can thus be manufactured, packaged, and delivered to the surgeon as a single unit. During an aortic valve/ascending aortic replacement procedure, a surgeon attaches the base of the prosthesis in the same manner as done with current prosthetic valves, i.e., the aortic root is excised, the prosthesis is attached to the normal tissue in the left ventricular outflow tract, and the coronary arteries are removed. Once the base of the prosthesis has been attached, the upper portion of the prosthesis is then attached to the ascending aorta or the aortic arch and each coronary artery is attached to an ostium or an ostium attachment ring in a sinus of the device or to an artificial vessel attached to the ostium or ostium attachment ring.

DETAILED DISCLOSURE OF THE INVENTION

Figure 1A:
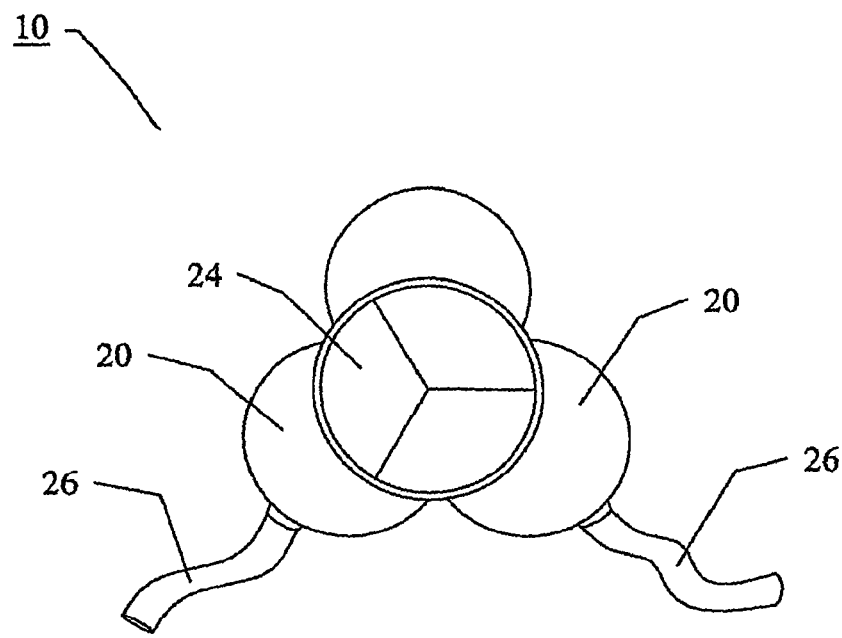
FIG. 1A is a schematic end view of a prosthetic device of the invention having vessels extending from the ostia.

The subject invention concerns vascular prostheses and methods for ascending aorta and aortic valve replacement in humans and animals. As shown in FIGS. 1A-1B and 2A-2B, exemplary embodiments of a vascular prosthesis 10 of the invention feature a vessel-like structure 14 that includes a first end 16 adapted for surgical attachment to a left ventricle, a second end 18 adapted for surgical attachment to an aorta, and interposed between the first and second end, a sinus portion 20 configured in the shape and size of a sinus of Valsalva in a human aorta. Sinus measurements for the sinus portion 20 can be determined from anatomic measurement of natural sinuses. In the embodiments shown in FIGS. 1A-1B and 2A-2B, the sinus portion 20 of the prosthesis 10 includes three sinus cavities, although it could include other numbers of cavities (e.g., 1, 2, 4, 5 or more). A sinus can optionally have an ostium 21 located thereon. As shown in the embodiment in FIG. 2B, two of the sinus cavities 20 shown each have an ostium 21 suitable for connecting a vessel 26 such as a coronary artery or an artificial or non-artificial vessel (as in the embodiment shown in FIGS. 1A and 1B) to which a coronary artery can be attached. The ostium 21 is provided at a location on a sinus for optimal fluid dynamics and blood flow. Each ostia can optionally have attached thereto an attachment ring 22 as shown in FIG. 1B. Attachment ring 22 can be used to provide an attachment point to assist in attaching a vessel 26 to a sinus. In one embodiment, the attachment ring 22 is composed of a biocompatible elastomeric material. In another embodiment, the attachment ring 22 comprises a polymer material that can be covered with a woven biocompatible material, such as DACRON (polyester).

The first 16 and/or second ends 18 of the vessel-like structure 14 are adapted for surgical attachment to the left ventricle and aorta, respectively. In one embodiment, the first end 16 and/or second end 18 comprise a sewing ring 28 encircling the end of the vessel-like structure 14 for suturing therethrough to attach the prosthesis 10 between the left ventricle and the remaining end of the aorta. In one embodiment, the sewing ring 28 is composed of a biocompatible elastomeric material. In another embodiment, the sewing ring 28 comprises a polymer material that can be covered with a woven biocompatible material, such as DACRON (polyester).

In embodiments where one or more artificial vessels are attached to the ostia (FIGS. 1A and 1B), suitable artificial vessels may be formed from any suitable biocompatible material (e.g., TEFLON, polyurethane, polyethylene, polytetrafluoroethylene (TFE) or other similar material). The artificial vessels may be synthetic or non-synthetic, or any combination thereof. The artificial vessels may be adapted to be coupled to one or more coronary arteries of a subject. The diameter and length of the artificial vessels is determined similar to the method described above for sinus size determination and would be sized to correspond with the diameter of the optimal coronary ostium. Non-artificial vessels that can be used include human venous or arterial conduit from the patient (such as a leg vein) or a cadaver or an animal of a species different from the patient. Vessels from a cadaver or another animal can be chemically preserved and treated to reduce antigenicity and/or thrombogenicity. An average measurement for a coronary artery is 2.5-3 mm and this measurement can be used as a starting point for artificial or non-artificial vessels used with a prosthesis of the invention.

Figure 1B:
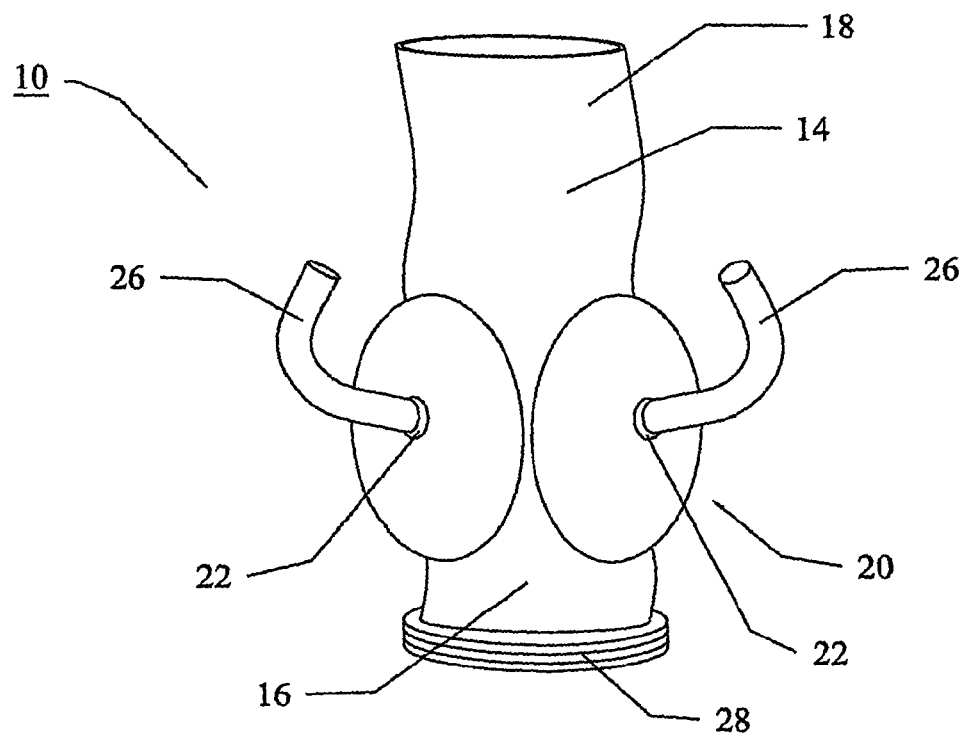
FIG. 1B is a schematic front view of a prosthetic device of FIG. 1A.
Figure 2A:
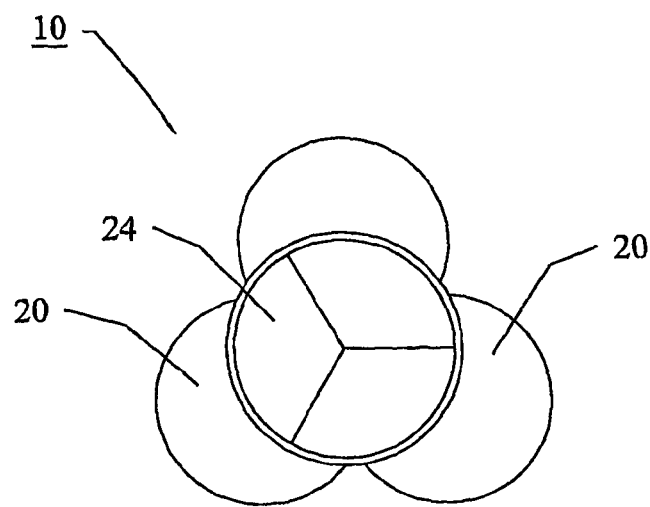
FIG. 2A is a schematic end view of a prosthetic device of the invention having ostia to which a vessel (e.g., a coronary artery) can be connected.
Figure 2B:
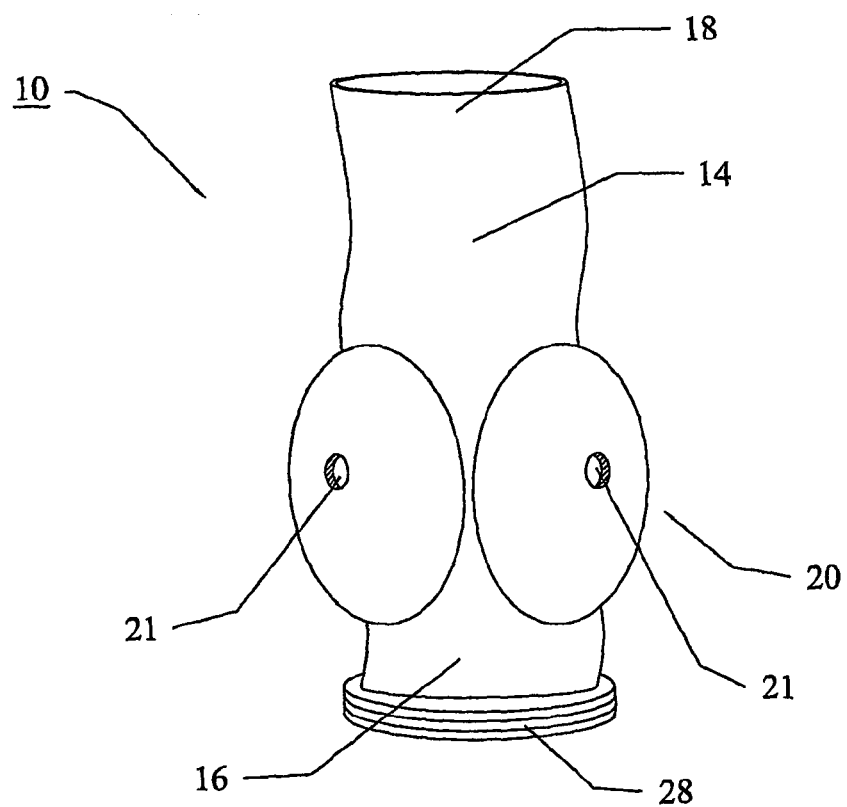
FIG. 2B is a schematic front view of a prosthetic device of FIG. 2A.
Figure 3A:
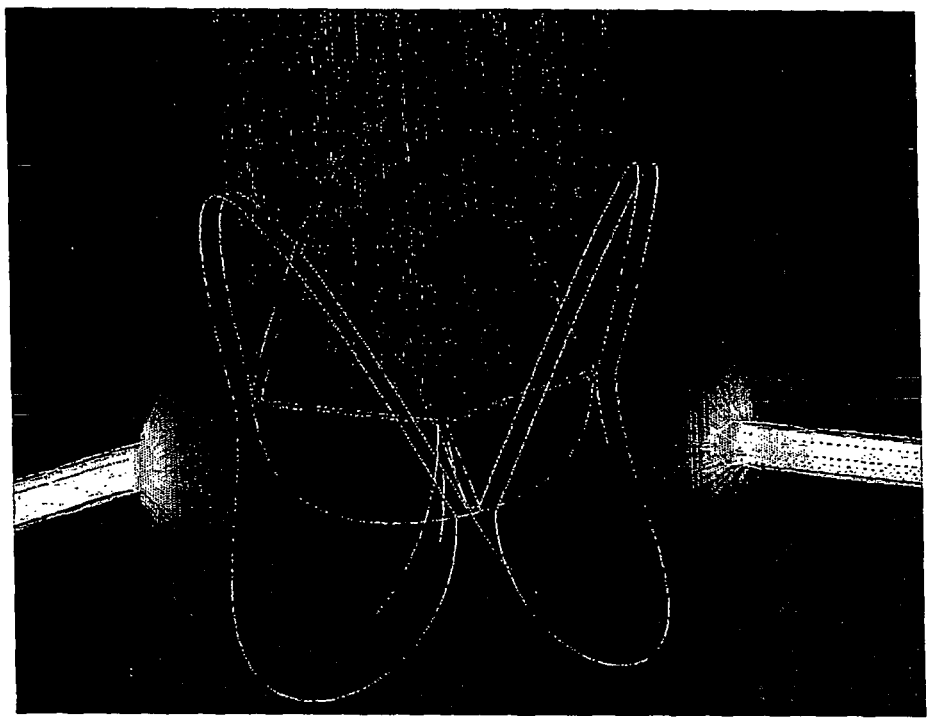
FIGS. 3A-D are a series of computer-generated images showing velocity streamlines of a prosthesis including sinuses (FIG. 3A) versus one without sinuses (FIG. 3B), and wall shear lines in a prosthesis including sinuses (FIG. 3C) versus one without sinuses (FIG. 3D).
Figure 3B:
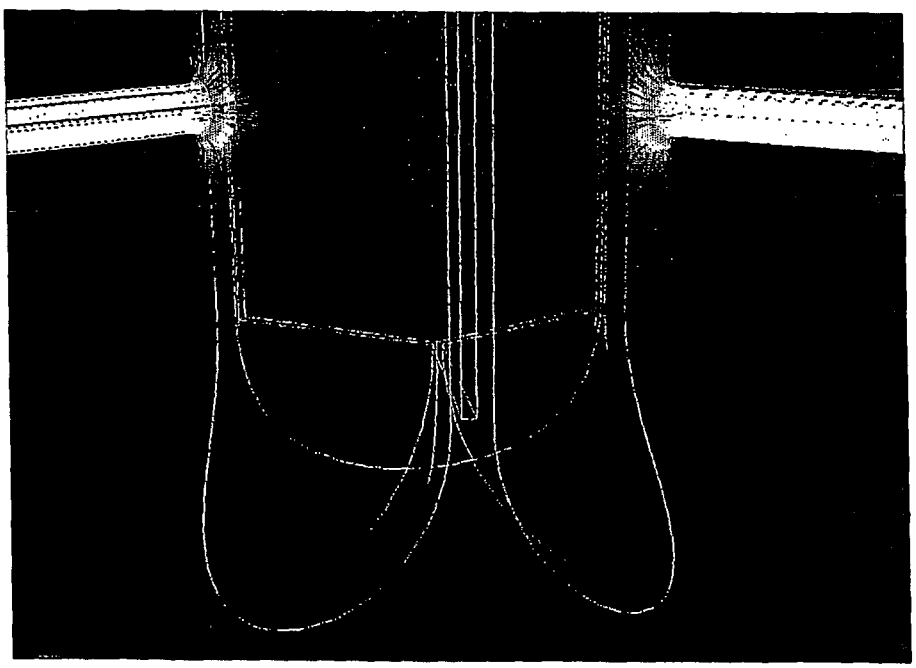
Figure 3C:
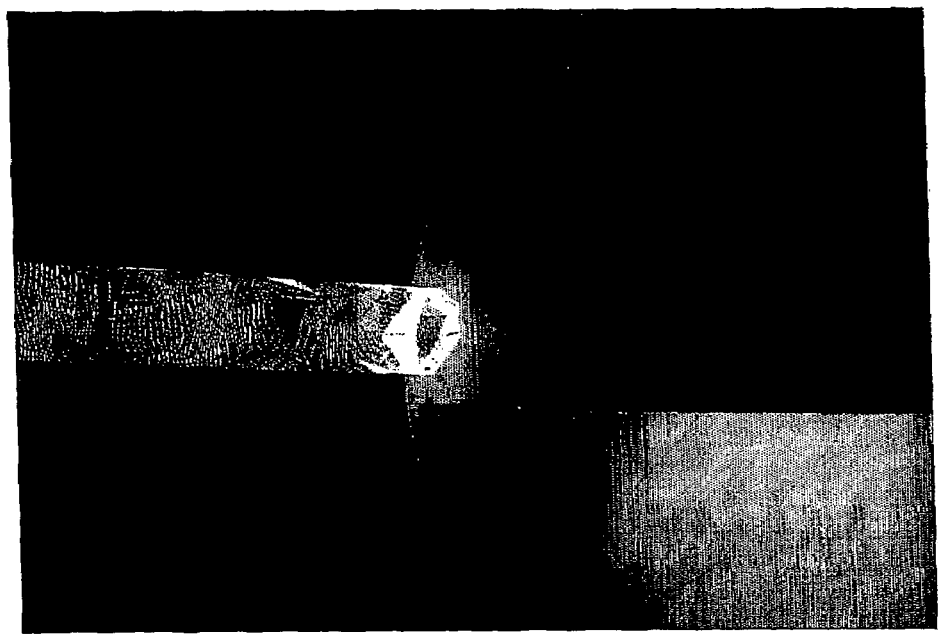
Figure 3D:
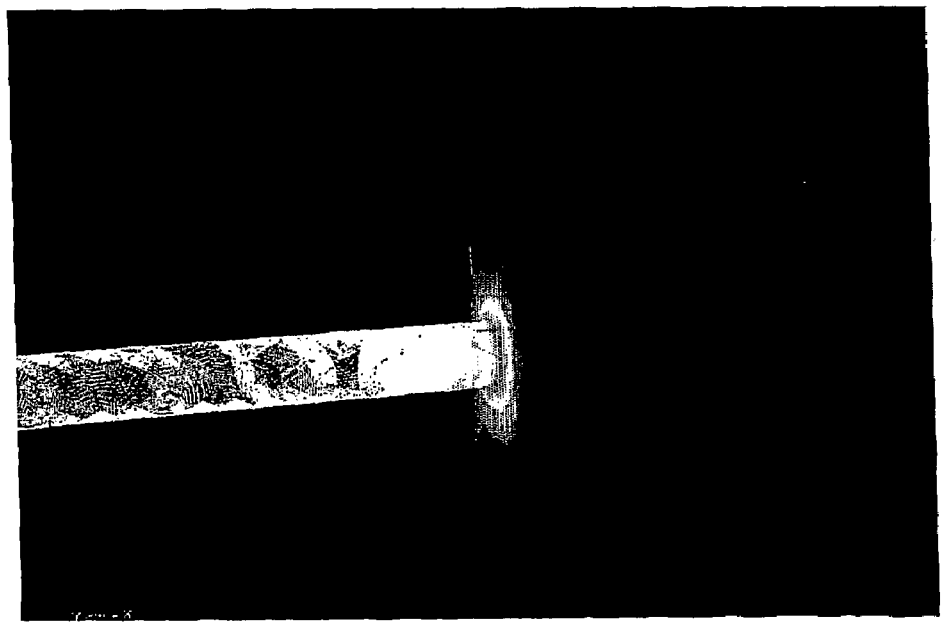

In one embodiment, a vascular prosthesis 10 of the invention, as shown in FIGS. 1A and 2A can also include a valve 24 for regulating fluid flow. The valve 24 is located toward the first end 16 of the vessel-like structure 14 so that it is proximal to the ventricle when implanted. The valve 24 can be a separate component that is inserted into the prosthesis or it can be integral with the prosthetic structure (i.e., formed as one unit with the rest of the vessel-like structure). Several suitable valves are known, including those used previously for aortic valve replacement. For example, the valve can be one formed from animal tissue. In another embodiment, the valve may be formed from synthetic or non-synthetic material, or any combination thereof. In one example, the valve may be formed from polyester, plastic, and/or metal or other similar material. Valves used with a device of the present invention can be of any form suitable for an aortic valve and include, but are not limited to a caged ball valve, a tilting disc valve, a bileaflet valve, or a trileaflet valve. In an exemplified embodiment, the valve is a trileaflet valve. If a bileaflet valve is used with a prosthesis of the invention, then typically the vessel-like structure 14 will comprise two sinus cavities 20. If a trileaflet valve is used, then three sinus cavities are typically present on the structure. Preferably, the number of sinus cavities on the prosthesis is equivalent to the number of leaflets of the valve and have the same basic angles and arch dimensions. Examples of valves are described in U.S. Pat. Nos. 6,461,382; 4,451,936; and 4,892,540.

Figure 4:
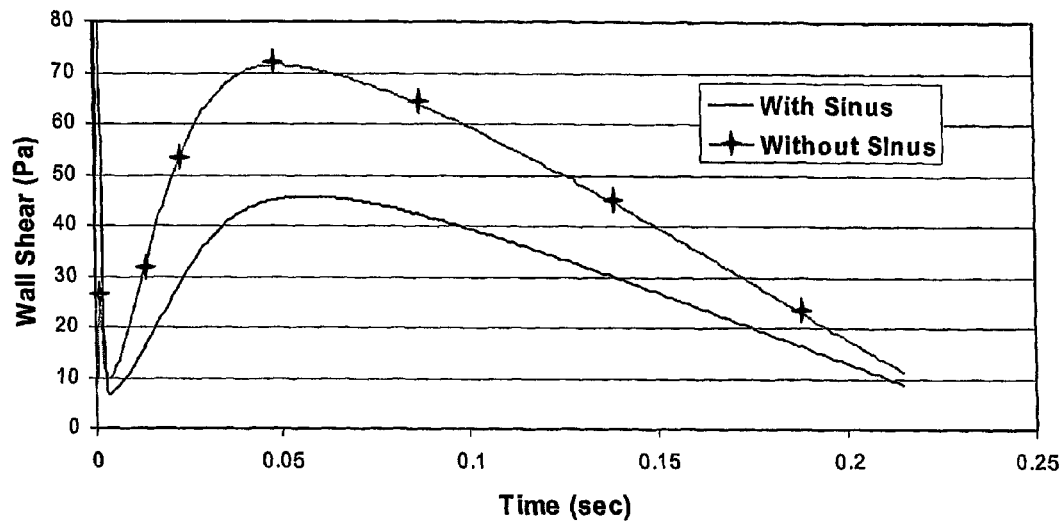
FIG. 4 is a graph of the wall shear versus time from a sinus-containing prosthesis versus one without sinuses.
Figure 5:
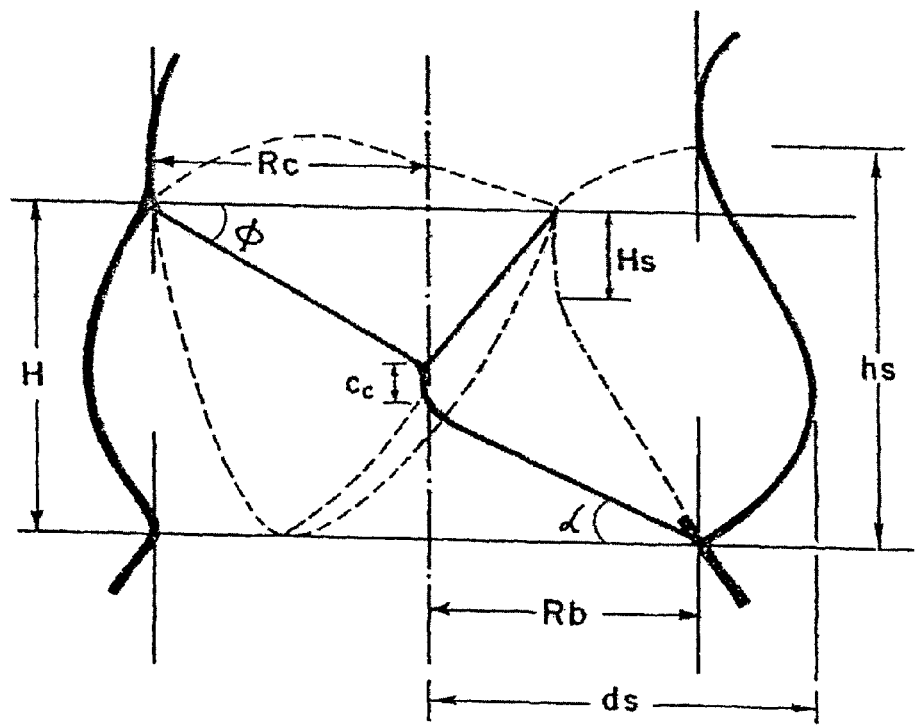
FIG. 5 is a diagram illustrating height of the sinuses (hs) measured to be 19.9-24.6 mm (1.76×Rb, with the mean Rb=11.3-14 mm). The distance the sinuses extend out from the normal lumen of the aortic valve ring can be measured by the total sinuses depth (ds) minus the radius of the base of the ring (Rb), namely 5.2-6.4 mm (ds−Rb; with ds=1.46× Rb=16.5 to 20.4).

Referring to FIG. 3, a computer modeling showed that a sinus-containing prosthesis having optimally located ostia exhibited better fluid dynamics than did a conventional prosthesis. Velocity streamlines of a prosthesis including sinuses are shown in FIG. 3A. Velocity streamlines of a prosthesis without sinuses is shown in FIG. 3B. Wall shear lines in a prosthesis including sinuses versus one without sinuses are shown in FIGS. 3C and 3D, respectively. These experiments showed that the prosthesis with sinuses and optimally placed ostia provides better flow and less wall shear than the prosthesis without sinuses. These results are also illustrated in the data shown in FIG. 4.

Optimal placement of each ostium 21 on the sinus cavities 20 for a particular application can be determined by any suitable means, including both cadaver measurements and/or computational fluid dynamic models based on correlations of certain coronary attachment sites and those individuals having associated cardiac procedures (e.g., quadruple and triple bypass surgery, pacemakers, etc.). In one embodiment, a computational fluid dynamics software package (CFX 5.7, ANSYS, Inc., Canonsburg, Pa.) is used to determine the most efficient attachment site (based from maximum fluid flow into coronaries, minimum wall shear, etc.). Optimal placement of the ostia was found to be in the range of about 10-20 mm or about 12-18 mm or about 14-16 mm or about 15 mm from the base of the sinus. The base is the portion of the sinus proximal to the ventricle that first starts to bulge.

The components of a prosthesis of the invention can be made of any suitable biocompatible material. Several are known in the art and include, but are not limited to, stainless steel, titanium or chromium, metal alloys, LEXAN (polycarbonate polymer), polysulfone, polyurethane, polytetrafluoroethylene (PTFE), DACRON, and other polyester-like materials etc. See The Aortic Valve by Mano J. Thubrikar and Peter P. Klemchuk, 1989, CRC Press, Boca Raton, Fla. In one embodiment, the prosthesis is constructed of a soft DACRON-like material. Published U.S. Patent Application 2002/0082689 describes a heart valve composed of polyurethane/polysiliconurethane blends. The components of a prosthesis of the invention, including the valve, can also be coated so as to render them more biocompatible. Published U.S. Patent Application 2001/0025196 describes a coating that can be applied to device components, particularly heart valves, that render the components more biocompatible. Components of a prosthesis of the present invention can be coated with one or more antibiotics. Antibiotics on the prosthesis help prevent bacterial infection after implantation in a patient. Any suitable antibiotic can be used with a prosthesis of the invention including, but not limited to, penicillin, tetracycline, erythromycin, streptomycin, gentamicin, ampicillin, and vancomycin. Components of a prosthesis of the invention can also be coated with compositions to make the components more hemostatic, to help present tissue overgrowth, etc. following implantation of a prosthesis (see, for example Published U.S. Patent Application Nos. 2004/0062790 and 2004/0093080). Compositions that can be coated on a component of the invention include, but are not limited to, an anticoagulant, an antithrombogenic agent, an antiproliferative agent, an antiplatelet agent, an antiinflammatory agent, an antioxidant, a pharmaceutical agent, etc. Components can be coated according to standard methods known in the art. For example, published U.S. Patent Application No. 2002/0071902 describes biostable polymeric material in which a biologically active material or composition is dispersed as a coating on a surface of an implantable device.

The size of the prosthesis will vary depending on the particular application. Generally, the prosthesis is sized to mimic the size of the corresponding components of the natural tissue being replaced. The sinuses may be of any size appropriate for the size of the subject to receive the prosthesis, and typically will be approximately the size of the sinuses in the tissue being replaced. In one embodiment, the size and geometry of the sinuses is based on normal, average measurements, for example those described in The Aortic Valve by Mano J. Thubrikar and Peter P. Klemchuk, 1989, CRC Press, Boca Raton, Fla. These normal average measurements can be used to construct a range of prostheses of different sizes from which a surgeon can choose the most appropriate size for the subject being treated.

The vascular prostheses of the present invention are designed for surgical implantation into an animal or human subject in need of replacement of an ascending aorta with or without concomitant aortic valve replacement. In an exemplary method of implanting the prosthesis in a subject, the subject is prepared for surgery as in conventional ascending aorta or aortic valve replacement surgery. For example, the subject is first anesthetized. The heart is then surgically exposed and arrested, and the subject is connected to a cardio-pulmonary (heart-lung) bypass machine. The defective ascending aorta and sinuses of Valsalva and/or the aortic valve are excised leaving the left ventricle and aorta unconnected, and the left and right coronary arteries are detached from the sinuses. The first end of the prosthesis is then surgically attached to the ventricle to close off the opening left by removal of the ascending aorta and original valve, and the second end of the prosthesis is attached to the distal end of the aorta. The coronary arteries are then attached to the ostia of the sinuses. In some embodiments, exemplified in FIGS. 1A-1B, artificial vessels or blood vessels from the patient, a cadaver, or another animal (e.g., pig (porcine) and cow (bovine)) are attached to and extend from the ostia and the coronary arteries are attached to these vessels. The heart is restarted, the cardio-pulmonary bypass terminated, and the surgical site closed.

The subject invention also concerns methods for replacement of a defective or damaged ascending aorta or aortic valve in humans or other animals. During an aortic valve replacement procedure, a surgeon attaches a prosthesis of the present invention with a valve of the surgeons choice, in the same manner as is done with current prosthetic valves, i.e., most of the aortic root is excised, the first end 16 of the prosthesis is attached to the normal tissue in the left ventricular outflow tract, and the coronary arteries are removed. The prosthesis 10 used in ascending aorta replacement does not have a valve 24. If only an ascending aorta is being replaced, then most of the aortic root is removed but the native aortic valve is left in place and the first end 16 of the prosthesis is attached to the normal tissue in the left ventricular outflow tract, and the coronary arteries are removed. Once the first end 16 of the prosthesis has been attached, the second end 18 of the prosthesis is then attached to the ascending aorta or aortic arch and each coronary artery is attached to an ostium 21, to an ostium attachment ring 22 or to a vessel 26 attached to the ostium.

Although the foregoing embodiments mainly relate to ascending aorta and aortic valve repair/replacements, this technology can also be applied to other valve replacement and vessel repair procedures. A prosthesis of the invention can also be used in treating a condition known as transposition of the great arteries. This is a congenital malformation in which the aorta is attached to the right ventricle instead of the left and the pulmonary artery is attached to the left ventricle instead of the right. These patients require the great vessels to be switched and the coronaries to be re-attached. There is often times problems with the re-attachment of the coronaries.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

REFERENCES

U.S. Pat. No. 6,461,382
U.S. Pat. No. 4,451,936
U.S. Pat. No. 4,892,540
Published U.S. Patent Application 2001/0025196
Published U.S. Patent Application 2002/0082689
Published U.S. Patent Application No. 2004/0093080
Published U.S. Patent Application No. 2002/0071902
Published U.S. Patent Application No. 2004/0062790
Thubrikar, Mano J. Klemchuk, Peter P. Klemchuk (1989) In The Aortic Valve. CRC Press, Boca Raton, Fla.

I claim:

1. A prosthesis comprising:
a vessel-like structure having a first end adapted for surgical attachment to a left ventricle, a second end adapted for surgical attachment to an aorta, and, interposed between the first and second ends, a sinus portion configured in the shape of the sinuses of Valsalva in a human aortic valve, wherein said vessel-like structure is composed of a synthetic material, and wherein said sinus portion comprises an ostium and attached to said ostium is an ostium attachment ring.

2. The prosthesis according to claim 1, wherein an artificial vessel is connected to said ostium.

3. The prosthesis according to claim 1, wherein said sinus portion comprises three sinus cavities.

4. The prosthesis according to claim 3, wherein at least two of said sinus cavities each comprise an ostium.

5. The prosthesis according to claim 4, wherein said ostium is located at a position on said sinus for optimal fluid dynamics and blood flow.

6. The prosthesis according to claim 5, wherein said ostium is located about 10 to 20 mm from the base of said sinus.

7. The prosthesis according to claim 5, wherein said ostium is located about 12 to 18 mm from the base of said sinus.

8. The prosthesis according to claim 5, wherein said ostium is located about 14 to 16 mm from the base of said sinus.

9. The prosthesis according to claim 5, wherein said ostium is located about 15 mm from the base of said sinus.

10. The prosthesis according to claim 4, wherein an artificial vessel is connected to said ostium.

11. The prosthesis according to claim 1, wherein said vessel-like structure further comprises a valve for regulating fluid flow.

12. The prosthesis according to claim 11, wherein said valve comprises animal tissue.

13. The prosthesis according to claim 11, wherein said valve does not comprise animal tissue.

14. The prosthesis according to claim 13, wherein said valve is a caged ball valve, a tilting disc valve, a bileaflet valve, or a trileaflet valve.

15. The prosthesis according to claim 1, wherein said first end or said second end or both said first end and said second end of said vessel-like structure comprise a sewing ring.

16. The prosthesis according to claim 15, wherein said sewing ring comprises a biocompatible elastomeric material.

17. The prosthesis according to claim 15, wherein said sewing ring comprises a polymer material.

18. The prosthesis according to claim 17, wherein said polymer material is covered with a woven biocompatible material.

19. The prosthesis according to claim 1, wherein an artificial or a non-artificial vessel is connected to said ostium attachment ring.

20. The prosthesis according to claim 1, wherein said ostium is located at a position on said sinus for optimal fluid dynamics and blood flow.

21. The prosthesis according to claim 20, wherein said ostium is located about 10 to 20 mm from the base of said sinus.

22. The prosthesis according to claim 20, wherein said ostium is located about 12 to 18 mm from the base of said sinus.

23. The prosthesis according to claim 20, wherein said ostium is located about 14 to 16 mm from the base of said sinus.

24. The prosthesis according to claim 20, wherein said ostium is located about 15 mm from the base of said sinus.

25. The prosthesis according to claim 1, wherein said vessel-like structure or a portion thereof is composed of a material selected from the group consisting of stainless steel, titanium, chromium, a metal alloy, polycarbonate polymer, polysulfone, polyurethane, polytetrafluoroethylene, and a blend of polyurethane and polysiliconurethane.

26. The prosthesis according to claim 1, wherein said vessel-like structure or a portion thereof comprises a coating to render said structure more biocompatible.

27. The prosthesis according to claim 1, wherein said vessel-like structure or a portion thereof comprises a coating comprising one or more compositions selected from the group consisting of an antibiotic, anticoagulant, antitlirombogenic, antiproliferative, antiplatelet, antiinflammatory, antioxidant, and a pharmaceutical agent.

28. The prosthesis according to claim 1, wherein said vessel-like structure or a portion thereof comprises a coating to render said structure more hemostatic.

29. A method for replacing an ascending aorta in a human or animal, the method comprising the step of:
   a) removing the ascending aorta present in the human or animal; and
   b) implanting the prosthesis of claim 1 into the human or animal.

* * * * *

UNITED STATES PATENT AND TRADEMARK OFFICE
CERTIFICATE OF CORRECTION

PATENT NO. : 7,431,733 B2  
APPLICATION NO. : 10/561929  
DATED : October 7, 2008  
INVENTOR(S) : Joseph Allen Knight Page 1 of 1

It is certified that error appears in the above-identified patent and that said Letters Patent is hereby corrected as shown below:

<u>Column 3,</u>
Line 33, "(TFE)" should read --PTFE)--.

<u>Column 8,</u>
Line 18, "antitlirombogenic" should read --antithrombogenic--.

Signed and Sealed this

Twenty-sixth Day of May, 2009

JOHN DOLL
*Acting Director of the United States Patent and Trademark Office*